(12) United States Patent
Zhu et al.

(10) Patent No.: US 10,975,157 B2
(45) Date of Patent: Apr. 13, 2021

(54) ANTI-OX40 ANTIBODIES AND DIAGNOSTIC USES THEREOF

(71) Applicant: Ventana Medical Systems, Inc., Tucson, AZ (US)

(72) Inventors: Yifei Zhu, San Jose, CA (US); Zhiming Liao, Livermore, CA (US); Robert Pytela, San Francisco, CA (US)

(73) Assignee: Ventana Medical Systems, Inc., Tucson, AZ (US)

(*) Notice: Subject to any disclaimer, the term of this patent is extended or adjusted under 35 U.S.C. 154(b) by 76 days.

(21) Appl. No.: 15/921,254

(22) Filed: Mar. 14, 2018

(65) Prior Publication Data

US 2018/0208666 A1 Jul. 26, 2018

Related U.S. Application Data

(63) Continuation of application No. PCT/EP2016/072236, filed on Sep. 20, 2016.

(60) Provisional application No. 62/222,105, filed on Sep. 22, 2015.

(51) Int. Cl.
*C07K 16/28* (2006.01)
*A61K 39/00* (2006.01)
*G01N 33/574* (2006.01)

(52) U.S. Cl.
CPC ....... *C07K 16/2878* (2013.01); *G01N 33/574* (2013.01); *A61K 2039/505* (2013.01); *C07K 2317/34* (2013.01); *C07K 2317/54* (2013.01); *C07K 2317/55* (2013.01); *C07K 2317/56* (2013.01); *C07K 2317/567* (2013.01); *C07K 2317/622* (2013.01); *C07K 2317/626* (2013.01); *G01N 2333/70578* (2013.01)

(58) Field of Classification Search
CPC ............ C07K 16/2878; C07K 2317/34; C07K 2317/54; C07K 2317/56; C07K 2317/622; C07K 2317/626; A61K 2039/505; G01N 33/574

See application file for complete search history.

(56) References Cited

U.S. PATENT DOCUMENTS

| | | | | |
|---|---|---|---|---|
| 6,528,623 B2 * | 3/2003 | Godfrey | ........... | C07K 14/70575 530/387.1 |
| 8,283,450 B2 * | 10/2012 | Kato | ................ | C07K 16/2878 530/387.3 |
| 2006/0190185 A1 | 8/2006 | Ford et al. | | |
| 2014/0162904 A1 | 6/2014 | Yu | | |

FOREIGN PATENT DOCUMENTS

| | | |
|---|---|---|
| JP | 2007086080 A | 4/2007 |
| JP | 2009518005 A | 5/2009 |
| JP | 2010518873 A | 6/2010 |
| WO | 2007062245 A2 | 12/2007 |
| WO | 2008106116 A2 | 10/2008 |

OTHER PUBLICATIONS

Bending, M.M. Humanization of rodent monoclonal antibodies by CDR grafting. Methods: A Companion to Methods in Enzymology, 1995, 8:83-93.*
Casset, F., et al. A peptide mimetic of an anti-CD4 monoclonal antibody by rational design. Biochem. Biophys. Res. Comm., 2003, 307:198-205.*
MacCallumm, R.M., et al. Antibody-antigen interactions: Contact analysis and binding site topography. J. Mol. Biol., 1996, 262:732-745.*
Paul, W.E., Fundamental Immunology, 3rd Edition, 1993, pp. 292-295.*
Rudikoff, S., et al. Single amino acid substitution altering antigen-binding specificty. Proc. Natl. Acad. Sci. USA, 1982, 79:1979-1983.*
Anonymous, Ox40 (BER-Act35): sc-20073, -, -, retrieved from the Internet https://datasheets.scbt.com/sc-20073.pdf, -, Santa Cruz Biotechnology, Inc.
BD Pharmingen, Purified Mouse Anti-Human CD134, Technical Data Sheet, (2006), URL:http://www.bdbiosciences.com/ds/pm/tds/555836.pdf, retrieved from the Internet.
Ilves, T. et al., OX40 ligand and OX40 are increased in atopic dermatitis lesions but do not correlate with clinical severity, JEADV, (2012), pp. e197-e205, vol. 27 No. 2.
International Search Report and Written Opinion dated Dec. 1, 2016 in corresponding PCT/EP2016/072236 filed Sep. 20, 2016, pp. 1-12.
Ramstad, T. et al., Immunohistochemical analysis of primary breast tumors and tumor-draining lymph nodes by means of the T-cell costimulatory molecule OX-40, The American Journal of Surgery, (2000), pp. 400-406, vol. 179 Issue 5.
Byun, M., et al., Inherited human OX40 deficiency underlying classic Kaposi sarcoma of childhood, The Journal of Experimental Medicine, 2013, pp. 1743-1759, vol. 210, No. 9.
Imura, A., et al., OX40 Expressed on Fresh Leukemic Cells From Adult T-Cell Leukemia Patients Mediates Cell Adhesion to Vascular Endothelial Cells: Implication for the Possible Involvement of OX40 in Leukemic Cell Infiltration, Blood, Apr. 15, 1997, pp. 2951-2958, vol. 89, No. 8.
Taylor, L., et al., Identification of a soluble OX40 isoform: development of a specific and quantitative immunoassay, Journal of Immunological Methods, 2001, pp. 67-72, vol. 255.

* cited by examiner

*Primary Examiner* — Daniel E Kolker
*Assistant Examiner* — Bruce D. Hissong
(74) *Attorney, Agent, or Firm* — Ventana Medical Systems, Inc.

(57) ABSTRACT

The invention provides antibodies immunoreactive with human OX40 and methods of using the same. The antibodies are reactive with a portion of the C-terminus of the human OX40 protein that includes amino acids 266-277. The antibodies are useful for detecting OX40 protein expression in human tissue samples, including by immunohistochemistry, immunofluorescence, or immunoblot.

24 Claims, 2 Drawing Sheets
(2 of 2 Drawing Sheet(s) Filed in Color)

Specification includes a Sequence Listing.

SEQUENCE LISTING

<160> NUMBER OF SEQ ID NOS: 17

<210> SEQ ID NO 1
<211> LENGTH: 277
<212> TYPE: PRT
<213> ORGANISM: Homo sapiens

<400> SEQUENCE: 1

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 2
<211> LENGTH: 5
<212> TYPE: PRT
<213> ORGANISM: Artificial Sequence
<220> FEATURE:
<223> OTHER INFORMATION: Fragment of a recombinant antibody

<400> SEQUENCE: 2

```
Ser Asp Asn Ile Gln
1               5
```

<210> SEQ ID NO 3

```
<211> LENGTH: 16
<212> TYPE: PRT
<213> ORGANISM: Artificial Sequence
<220> FEATURE:
<223> OTHER INFORMATION: Fragment of a recombinant antibody

<400> SEQUENCE: 3

Ala Val Asp Tyr Asn Asn Lys Pro Phe Tyr Ala Asn Trp Ala Lys Gly
1               5                   10                  15

<210> SEQ ID NO 4
<211> LENGTH: 5
<212> TYPE: PRT
<213> ORGANISM: Artificial Sequence
<220> FEATURE:
<223> OTHER INFORMATION: Fragment of a recombinant antibody

<400> SEQUENCE: 4

Asn Thr Phe Ser Pro
1               5

<210> SEQ ID NO 5
<211> LENGTH: 29
<212> TYPE: PRT
<213> ORGANISM: Artificial Sequence
<220> FEATURE:
<223> OTHER INFORMATION: Fragment of a recombinant antibody

<400> SEQUENCE: 5

Gln Ser Leu Glu Glu Ser Gly Gly Arg Leu Val Ala Pro Gly Gly Ser
1               5                   10                  15

Leu Thr Leu Thr Cys Thr Val Ser Gly Ile Asp Leu Ser
            20                  25

<210> SEQ ID NO 6
<211> LENGTH: 14
<212> TYPE: PRT
<213> ORGANISM: Artificial Sequence
<220> FEATURE:
<223> OTHER INFORMATION: Fragment of a recombinant antibody

<400> SEQUENCE: 6

Trp Val Arg Gln Ala Pro Gly Lys Gly Leu Glu Trp Ile Gly
1               5                   10

<210> SEQ ID NO 7
<211> LENGTH: 31
<212> TYPE: PRT
<213> ORGANISM: Artificial Sequence
<220> FEATURE:
<223> OTHER INFORMATION: Fragment of a recombinant antibody

<400> SEQUENCE: 7

Arg Phe Thr Ile Ser Lys Thr Ser Ser Thr Thr Val Asp Leu Lys Met
1               5                   10                  15

Thr Ser Leu Thr Thr Glu Asp Thr Ala Thr Tyr Phe Cys Ala Lys
            20                  25                  30

<210> SEQ ID NO 8
<211> LENGTH: 11
<212> TYPE: PRT
<213> ORGANISM: Artificial Sequence
<220> FEATURE:
<223> OTHER INFORMATION: Fragment of a recombinant antibody

<400> SEQUENCE: 8
```

```
Trp Gly Pro Gly Thr Leu Val Thr Val Ser Ser
1               5                   10
```

<210> SEQ ID NO 9
<211> LENGTH: 13
<212> TYPE: PRT
<213> ORGANISM: Artificial Sequence
<220> FEATURE:
<223> OTHER INFORMATION: Fragment of a recombinant protein

<400> SEQUENCE: 9

```
Gln Ser Ser Gln Ser Val Tyr Asn Ala Asn His Leu Ser
1               5                   10
```

<210> SEQ ID NO 10
<211> LENGTH: 7
<212> TYPE: PRT
<213> ORGANISM: Artificial Sequence
<220> FEATURE:
<223> OTHER INFORMATION: Fragment of a recombinant antibody

<400> SEQUENCE: 10

```
Tyr Ile Ser Thr Pro Asp Ser
1               5
```

<210> SEQ ID NO 11
<211> LENGTH: 11
<212> TYPE: PRT
<213> ORGANISM: Artificial Sequence
<220> FEATURE:
<223> OTHER INFORMATION: Fragment of a recombinant antibody

<400> SEQUENCE: 11

```
Cys Ala Ala Leu Asn Ser Asp Glu Val Phe Thr
1               5                   10
```

<210> SEQ ID NO 12
<211> LENGTH: 23
<212> TYPE: PRT
<213> ORGANISM: Artificial Sequence
<220> FEATURE:
<223> OTHER INFORMATION: Fragment of a recombinant antibody

<400> SEQUENCE: 12

```
Asp Pro Ala Met Thr Gln Thr Pro Ser Ser Thr Ser Ala Ala Val Gly
1               5                   10                  15

Gly Thr Val Thr Ile Asn Cys
            20
```

<210> SEQ ID NO 13
<211> LENGTH: 15
<212> TYPE: PRT
<213> ORGANISM: Artificial Sequence
<220> FEATURE:
<223> OTHER INFORMATION: Fragment of a recombinant antibody

<400> SEQUENCE: 13

```
Trp Phe Gln Gln Lys Pro Gly Gln Pro Pro Lys Arg Leu Ile Tyr
1               5                   10                  15
```

<210> SEQ ID NO 14
<211> LENGTH: 31
<212> TYPE: PRT
<213> ORGANISM: Artificial Sequence
<220> FEATURE:
<223> OTHER INFORMATION: Fragment of a recombinant antibody

```
<400> SEQUENCE: 14

Gly Val Pro Pro Arg Phe Ser Gly Ser Gly Ser Gly Thr Gln Phe Thr
1               5                   10                  15

Leu Thr Ile Ser Gly Val Gln Cys Asp Asp Ala Ala Thr Tyr Tyr
            20                  25                  30

<210> SEQ ID NO 15
<211> LENGTH: 10
<212> TYPE: PRT
<213> ORGANISM: Artificial Sequence
<220> FEATURE:
<223> OTHER INFORMATION: Fragment of a recombinant antibody

<400> SEQUENCE: 15

Phe Gly Gly Gly Thr Glu Val Val Val Lys
1               5                   10

<210> SEQ ID NO 16
<211> LENGTH: 111
<212> TYPE: PRT
<213> ORGANISM: Artificial Sequence
<220> FEATURE:
<223> OTHER INFORMATION: Fragment of a recombinant antibody

<400> SEQUENCE: 16

Gln Ser Leu Glu Glu Ser Gly Gly Arg Leu Val Ala Pro Gly Gly Ser
1               5                   10                  15

Leu Thr Leu Thr Cys Thr Val Ser Gly Ile Asp Leu Ser Ser Asp Asn
            20                  25                  30

Ile Gln Trp Val Arg Gln Ala Pro Gly Lys Gly Leu Glu Trp Ile Gly
        35                  40                  45

Ala Val Asp Tyr Asn Asn Lys Pro Phe Tyr Ala Asn Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Lys Asn
                85                  90                  95

Thr Phe Ser Pro Trp Gly Pro Gly Thr Leu Val Thr Val Ser Ser
            100                 105                 110

<210> SEQ ID NO 17
<211> LENGTH: 110
<212> TYPE: PRT
<213> ORGANISM: Artificial Sequence
<220> FEATURE:
<223> OTHER INFORMATION: Fragment of a recombinant antibody

<400> SEQUENCE: 17

Asp Pro Ala Met Thr Gln Thr Pro Ser Ser Thr Ser Ala Ala Val Gly
1               5                   10                  15

Gly Thr Val Thr Ile Asn Cys Gln Ser Ser Gln Ser Val Tyr Asn Ala
            20                  25                  30

Asn His Leu Ser Trp Phe Gln Gln Lys Pro Gly Gln Pro Pro Lys Arg
        35                  40                  45

Leu Ile Tyr Tyr Ile Ser Thr Pro Asp Ser Gly Val Pro Pro Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Ala Leu Asn Ser Asp
                85                  90                  95
```

```
Glu Val Phe Thr Phe Gly Gly Gly Thr Glu Val Val Val Lys
            100                 105                 110
```

ANTI-OX40 ANTIBODIES AND DIAGNOSTIC USES THEREOF

CROSS-REFERENCE TO RELATED APPLICATIONS

This is a continuation of PCT/EP2016/072236, filed Sep. 20, 2016, and claims the benefit of U.S. Provisional Patent Application 62/222,105, filed Sep. 22, 2015, the content of each of which is incorporated by reference in its entirety.

SEQUENCE LISTING INCORPORATION BY REFERENCE

A sequence listing submitted herewith in a computer-readable format, having a file name of 33058US1_ST25.txt, created on Mar. 13, 2018, which is 8,570 bytes in size, is hereby incorporated-by-reference.

BACKGROUND OF THE INVENTION

Field of the Invention

The present invention relates to antibodies reactive with human OX40 (anti-OX40) and methods of using the same.

Brief Description of Related Art

OX40 is a 277 amino acid single pass type I membrane protein that functions as a receptor for Tumor necrosis factor ligand superfamily member 4 ligand (also called OX40L and CD252). Activation of OX40 has been shown increase their proliferation, survival, and effector function of cytotoxic T-lymphocytes. Curti et al., Cancer Res., Vol. 73, Issue 24, pp. 7189-98 (Oct. 31, 2013). Clinical trials are currently underway testing anti-OX40 antibodies in patients with advanced cancers to determine whether it is a useful target for potentiation of anti-tumor immune responses.

SUMMARY

The present disclosure relates to anti-OX40 antibodies and methods of using the same.

In one aspect, an antibody, antigen-binding fragment thereof, or a recombinant protein thereof is disclosed, wherein the antibody is capable of specifically binding to OX40.

In one aspect, an antibody, antigen-binding fragment thereof, or a recombinant protein thereof is disclosed, wherein the antibody is capable of specifically binding to amino acids 266-277 of SEQ ID NO: 1.

In one aspect, an antibody, antigen-binding fragment thereof, or a recombinant protein thereof is disclosed, wherein the antibody is capable of specifically binding to OX40, wherein the antibody binds to an epitope comprising 266-277 of human OX40 polypeptide (SEQ ID NO: 1). In some embodiments, the antibody comprises the following hypervariable regions (HVRs): (a) an HVR-H1 comprising the amino acid sequence of SDNIQ (SEQ ID NO: 2); (b) an HVR-H2 comprising the amino acid sequence of AVDYNNKPFYANWAKG (SEQ ID NO: 3); and (c) an HVR-H3 comprising the amino acid sequence of NTFSP (SEQ ID NO: 4). In some embodiments, the antibody further comprises the following heavy chain variable domain framework regions (FRs): (a) FR-H1 comprising the amino acid sequence of QSLEESGGRLVAPGGSLTLTCTVSGIDLS (SEQ ID NO: 5); (b) FR-H2 comprising the amino acid sequence of WVRQAPGKGLEWIG (SEQ ID NO: 6); (c) FR-H3 comprising the amino acid sequence of RFTISKTSSTTVDLKMTSLTTEDTATYFCAK (SEQ ID NO: 7); and (d) FR-H4 comprising the amino acid sequence of WGPGTLVTVSS (SEQ ID NO: 8). In some embodiments, the antibody further comprises the following HVRs: (a) an HVR-L1 comprising the amino acid sequence of QSSQSVYNANHLS (SEQ ID NO: 9); (b) an HVR-L2 comprising the amino acid sequence of YISTPDS (SEQ ID NO: 10); and (c) an HVR-L3 comprising the amino acid sequence of CAALNSDEVFT (SEQ ID NO: 11). In some embodiments, the antibody further comprises the following light chain variable domain FRs: (a) FR-L1 comprising the amino acid sequence of DPAMTQTPSSTSAAVGGTVTINC (SEQ ID NO: 12); (b) FR-L2 comprising the amino acid sequence of WFQQKPGQPPKRLIY (SEQ ID NO: 13); (c) FR-L3 comprising the amino acid sequence of GVPPRFSGSGSGTQFTLTISGVQCDDAATYY (SEQ ID NO: 14); and (d) FR-L4 comprising the amino acid sequence of FGGGTEVVVK (SEQ ID NO: 15). In some embodiments, the antibody comprises (a) a VH sequence having at least 95% sequence identity to the amino acid sequence of SEQ ID NO: 16; (b) a VL sequence having at least 95% sequence identity to the amino acid sequence of SEQ ID NO: 17; or (c) a VH sequence as in (a) and a VL sequence as in (b). In some embodiments, the antibody comprises a VH sequence of SEQ ID NO: 16. In some embodiments, the antibody comprises a VL sequence of SEQ ID NO: 17.

In other embodiments, the antibody comprises the following HVRs: (a) an HVR-L1 comprising the amino acid sequence of SEQ ID NO: 9; (b) an HVR-L2 comprising the amino acid sequence of SEQ ID NO: 10; and (c) an HVR-L3 comprising the amino acid sequence of SEQ ID NO: 11. In some embodiments, the antibody further comprises the following light chain variable domain FRs: (a) FR-L1 comprising the amino acid sequence of SEQ ID NO: 12; (b) FR-L2 comprising the amino acid sequence of SEQ ID NO: 13; (c) FR-L3 comprising the amino acid sequence of SEQ ID NO: 14; and (d) FR-L4 comprising the amino acid sequence of SEQ ID NO: 15.

In another aspect, the invention features an isolated antibody that specifically binds OX40, wherein the antibody comprises the following HVRs: (a) an HVR-H1 comprising the amino acid sequence of SEQ ID NO: 2; (b) an HVR-H2 comprising the amino acid sequence of SEQ ID NO: 3; (c) an HVR-H3 comprising the amino acid sequence of SEQ ID NO: 4; (d) an HVR-L1 comprising the amino acid sequence of SEQ ID NO: 9; (e) an HVR-L2 comprising the amino acid sequence of SEQ ID NO: 10; and (f) an HVR-L3 comprising the amino acid sequence of SEQ ID NO: 11. In some embodiments, the antibody further comprises the following heavy chain variable domain and light chain variable domain FRs: (a) FR-H1 comprising the amino acid sequence of SEQ ID NO: 5; (b) FR-H2 comprising the amino acid sequence of SEQ ID NO: 6; (c) FR-H3 comprising the amino acid sequence of SEQ ID NO: 7; (d) FR-H4 comprising the amino acid sequence of SEQ ID NO: 8; (e) FR-L1 comprising the amino acid sequence of SEQ ID NO: 12; (f) FR-L2 comprising the amino acid sequence of SEQ ID NO: 13; (g) FR-L3 comprising the amino acid sequence of SEQ ID NO: 14; and (h) FR-L4 comprising the amino acid sequence of SEQ ID NO: 15. In some embodiments, the antibody comprises a VH sequence of SEQ ID NO: 16 and a VL sequence of SEQ ID NO: 17.

In another aspect, the invention features an isolated antibody that competes for binding to OX40 with any one of the preceding antibodies.

In another aspect, the invention features an isolated antibody that binds to the same epitope as any one of the preceding antibodies.

In some embodiments, any one of the preceding antibodies can be a monoclonal antibody. In some embodiments, the monoclonal antibody can be a rabbit monoclonal antibody.

In some embodiments, any one of the preceding antibodies can be an IgG antibody (e.g., an IgG1 antibody).

In some embodiments, any one of the preceding antibodies can be an antibody fragment that specifically binds OX40. In some embodiments, the antibody fragment is selected from the group consisting of Fab, single chain variable fragment (scFv), Fv, Fab', Fab'-SH, F(ab')2, and diabody.

In another aspect, the invention features an immunoconjugate comprising any one of the preceding antibodies.

In another aspect, the invention features an isolated nucleic acid that encodes any of the antibodies described herein. In another aspect, the invention features a vector (e.g., an expression vector) comprising the nucleic acid for expressing the antibody. In another aspect, the invention features host cells comprising the preceding nucleic acids and/or vectors.

In some aspects, any one of the preceding antibodies can be for use in detecting the presence or expression level of OX40 in a biological sample. In some embodiments, the detecting is by immunohistochemistry (IHC), immunofluorescence (IF), or immunoblot. In some embodiments, the detecting is by IHC. In some embodiments, the sample comprises a fixed tissue. In some embodiments, the fixed tissue is a formalin-fixed paraffin-embedded (FFPE) tissue. In some embodiments, the sample is from a subject having, or predisposed to, cancer or an autoimmune disease.

A further aspect of the invention is a method of detecting the presence or expression level of OX40 in a biological sample comprising contacting the biological sample with any one of the preceding antibodies and detecting the presence of the bound antibody. In some embodiments, the detecting is by IHC, IF, or immunoblot. In some embodiments, the detecting is by IHC. In some embodiments, the sample comprises a fixed tissue. In some embodiments, the fixed tissue is a FFPE tissue. In some embodiments, the sample is from a subject having or predisposed to cancer or autoimmune disease.

BRIEF DESCRIPTION OF THE DRAWINGS

The application file contains at least one drawing executed in color. Copies of this patent or patent application with color drawings will be provided by the Office upon request and payment of the necessary fee.

DETAILED DESCRIPTION OF EMBODIMENTS OF THE INVENTION

I. Definitions

Figure 1:
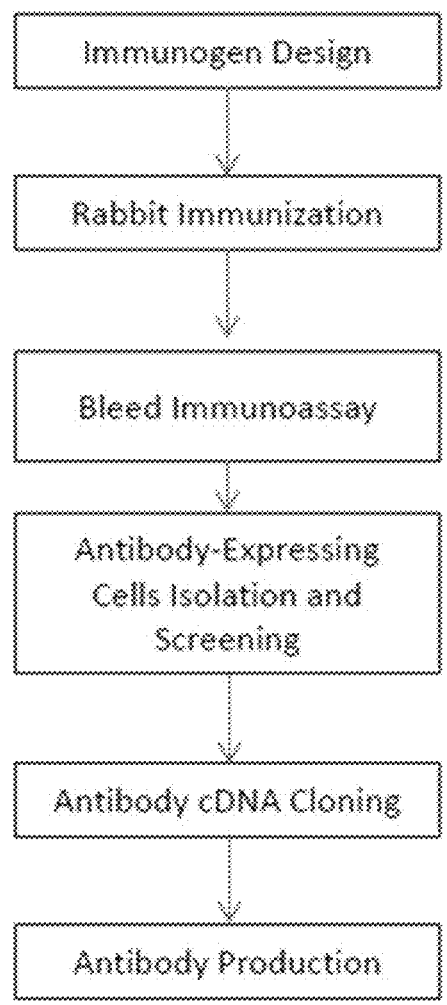
FIG. 1 is a schematic diagram showing the general antibody production process for the anti-OX40 antibody.
Figure 2:
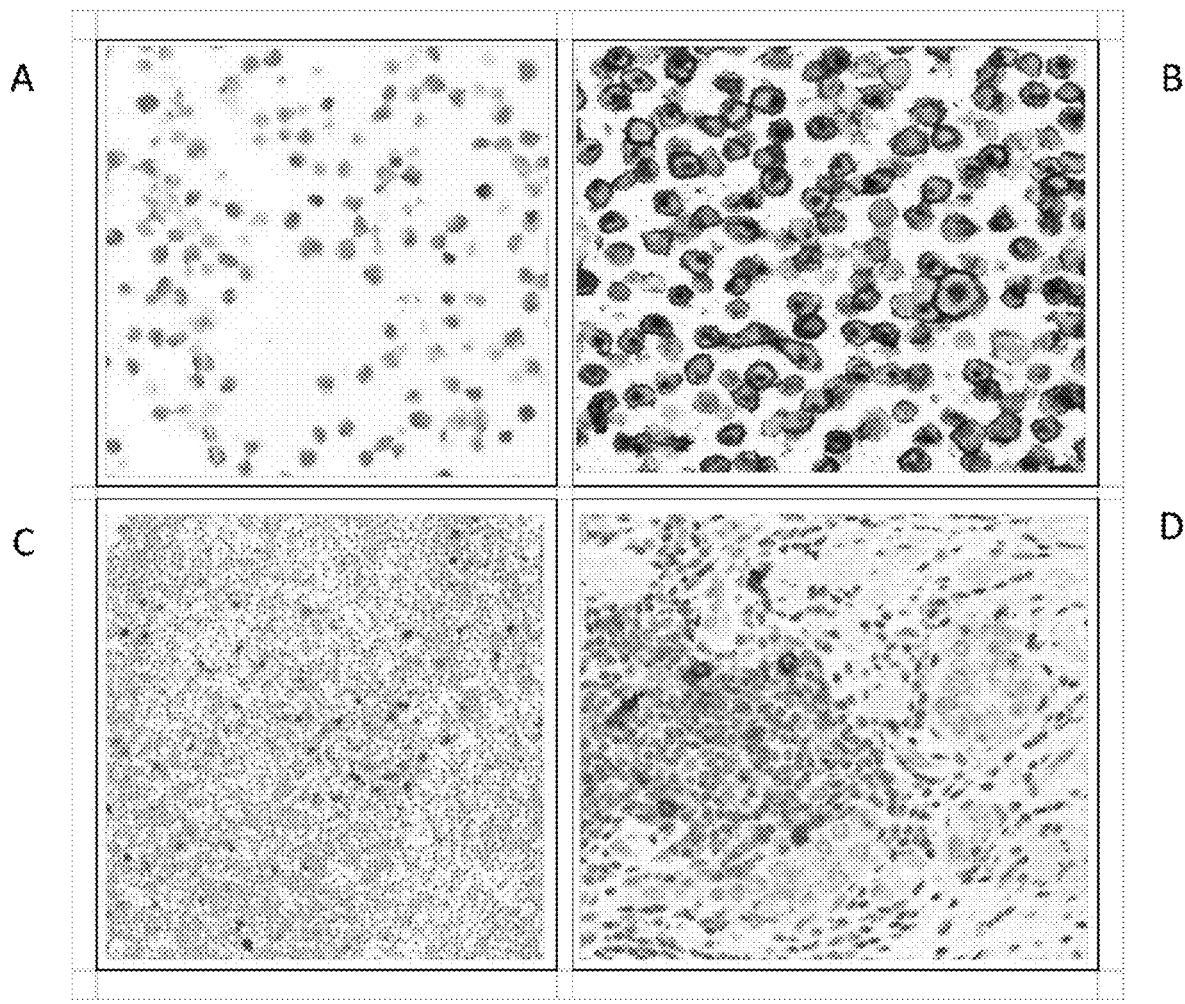
FIG. 2 is an image showing the results of immunohistochemistry (IHC) on formalin-fixed, paraffin-Embedded (FFPE) cells as follows: (A) Mock transfected cells (negative control cells); (B) OX-40 transfected cells (positive control cells); (C) Reactive lymph node; and (D) Prostate adenocarcinoma.

The terms "anti-OX40 antibody," "anti-OX40 antibody," "antibody that specifically binds to OX40," and "antibody that binds to OX40" refer to an antibody that is capable of binding OX40 with sufficient affinity such that the antibody is useful as a diagnostic and/or therapeutic agent in targeting OX40. In one embodiment, the extent of binding of an anti-OX40 antibody to an unrelated, non-OX40 protein is less than about 10% of the binding of the antibody to OX40 as measured, e.g., by a radioimmunoassay (RIA). In certain embodiments, an antibody that binds to OX40 has a dissociation constant (Kd) of ≤1 µM, ≤100 nM, ≤10 nM, ≤1 nM, ≤0.1 nM, ≤0.01 nM, or ≤0.001 nM (e.g., $10^{-8}$M or less, e.g., from $10^{-8}$ M to $10^{-13}$ M, e.g., from $10^{-9}$M to $10^{-13}$ M). In certain embodiments, an anti-OX40 antibody binds to an epitope of OX40 that is conserved among OX40 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

An "autoimmune disease" is a disease or disorder arising from and directed against an individual's own tissues or organs or a co-segregation or manifestation thereof or resulting condition therefrom. Autoimmune diseases can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis (RA), polymyositis, etc.). Non-limiting exemplary autoimmune diseases include autoimmune rheumatologic disorders (such as, for example, RA, Sjogren's syndrome, scleroderma, lupus such as SLE and lupus nephritis, polymyositis-dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, multiple sclerosis, Sjogren's syndrome, Graves' disease, IDDM, pernicious anemia, thyroiditis, and glomerulonephritis.

By "biological sample" is meant a collection of similar cells obtained from a subject or patient. A biological sample can be a tissue or a cell sample. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The biological sample can also be obtained from in vitro tissue or cell culture. The tissue sample may contain compounds which are not naturally intermixed with the tissue in nature such as preservatives, anticoagulants, buffers, fixatives, nutrients, antibiotics, or the like. Examples of biological samples herein include, but are not limited to, tumor biopsies, circulating tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. *Sequences of Proteins of Immunological Interest.* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

The terms "level of expression" or "expression level" in general are used interchangeably and generally refer to the amount of a polynucleotide, mRNA, or an amino acid product or protein in a biological sample. "Expression" generally refers to the process by which gene-encoded information is converted into the structures present and operating in the cell. Therefore, according to the invention "expression" of a gene (e.g., the OX40 gene) may refer to transcription into a polynucleotide, translation into a protein, or even posttranslational modification of the protein. Fragments of the transcribed polynucleotide, the translated protein, or the post-translationally modified protein shall also be regarded as expressed whether they originate from a transcript generated by alternative splicing or a degraded transcript, or from a post-translational processing of the protein, e.g., by proteolysis. In some embodiments, "expression level" refers to amount of a protein (e.g., OX40) in a biological sample as determined using immunohistochemistry (IHC), immunoblotting (e.g., Western blotting), immunofluorescence (IF), Enzyme-Linked Immunosorbant Assay (ELISA), or flow cytometry.

The terms "host cell," "host cell line," and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*. Fifth Edition, NIH Publication 91-3242, Bethesda Md., Vols. 1-3, 1991. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
(a) hypervariable loops occurring at amino acid residues 26-32 (L1), 50-52 (L2), 91-96 (L3), 26-32 (H1), 53-55 (H2), and 96-101 (H3) (Chothia et al. *J. Mol. Biol.* 196: 901-917, 1987);
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*. 5th Ed. Public Health Service, National Institutes of Health, Bethesda, Md., 1991);
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745, 1996); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3). Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al. *J. Chromatogr. B.* 848: 79-87, 2007.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-OX40 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "OX40," as used herein, refers to any native OX40 from any vertebrate source, including mammals such as primates (e.g., humans) and rodents (e.g., mice and rats), unless otherwise indicated. The term encompasses "full-length," unprocessed OX40 as well as any form of OX40 that results from processing in the cell. The term also encompasses naturally occurring variants of OX40, e.g., splice variants or allelic variants. The amino acid sequence of an exemplary full-length human OX40 protein is shown in SEQ ID NO: 1. The amino acid sequence of an exemplary full-length human OX40 protein can be found, e.g., under UniProt Accession No. P43489.

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope, e.g., amino acid residues 266-277 of SEQ ID NO: 1) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

A "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al. *Kuby Immunology*. 6th ed., page 91, W.H. Freeman and Co., 2007. A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al. *J. Immunol.* 150: 880-887, 1993 and Clarkson et al. *Nature.* 352: 624-628, 1991.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

The invention provides novel antibodies that bind to OX40. Antibodies of the invention are useful, for example, for detecting the presence of OX40 or the expression level of OX40 (e.g., in biological samples).

A. Exemplary Anti-OX40 Antibodies

The invention provides anti-OX40 antibodies useful for, e.g., diagnostic applications (e.g., immunohistochemistry (IHC), immunofluorescence (IF), and immunoblot (e.g., Western blot)). In one example, the invention provides anti-OX40 antibodies that bind to an a C-terminal epitope of OX40 (e.g., amino acid residues 266-277 SEQ ID NO: 1). The epitope on OX40 may be recognized in a manner that is conformation-dependent or conformation-independent.

In some instances, the anti-OX40 antibodies that bind to amino acid residues 266-277 of OX40 include at least one, two, three, four, five, or six HVRs selected from (a) HVR-H1 comprising the amino acid sequence of SEQ ID NO: 2; (b) HVR-H2 comprising the amino acid sequence of SEQ ID NO: 3; (c) HVR-H3 comprising the amino acid sequence of SEQ ID NO: 4; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. For example, in some instances, the anti-OX40 antibodies include (a) an HVR-H1 comprising the amino acid sequence of SEQ ID NO: 2; (b) an HVR-H2 comprising the amino acid sequence of SEQ ID NO: 3; and (c) an HVR-H3 comprising the amino acid sequence of SEQ ID NO: 4. In some instances, the anti-OX40 antibodies include (a) an HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In some instances wherein the anti-OX40 antibodies bind to amino acid residues 266-277 of OX40 and include (a) an HVR-H1 comprising the amino acid sequence of SEQ ID NO: 2; (b) an HVR-H2 comprising the amino acid sequence of SEQ ID NO: 3; and (c) an HVR-H3 comprising the amino acid sequence of SEQ ID NO: 4, the anti-OX40 antibodies further include the following heavy chain variable domain framework regions (FRs): (a) FR-H1 comprising the amino acid sequence of SEQ ID NO: 5; (b) FR-H2 comprising the amino acid sequence of SEQ ID NO: 6; (c) FR-H3 comprising the amino acid sequence of SEQ ID NO: 7; or (d) FR-H4 comprising the amino acid sequence of SEQ ID NO: 8. In some instances wherein the anti-OX40 antibodies bind to amino acid residues 266-277 of OX40 and include (a) an HVR-H1 comprising the amino acid sequence of SEQ ID NO: 2; (b) an HVR-H2 comprising the amino acid sequence of SEQ ID NO: 3; and (c) an HVR-H3 comprising the amino acid sequence of SEQ ID NO: 4, the anti-OX40 antibodies further include the following heavy chain variable domain framework regions (FRs): (a) FR-H1 comprising the amino acid sequence of SEQ ID NO: 5; (b) FR-H2 comprising the amino acid sequence of SEQ ID NO: 6; (c) FR-H3 comprising the amino acid sequence of SEQ ID NO: 7; and (d) FR-H4 comprising the amino acid sequence of SEQ ID NO: 8.

In some instances wherein the anti-OX40 antibodies bind to amino acid residues 266-277 of OX40, the antibodies include (a) an HVR-H1 comprising the amino acid sequence of SEQ ID NO: 2; (b) an HVR-H2 comprising the amino acid sequence of SEQ ID NO: 3; (c) an HVR-H3 comprising the amino acid sequence of SEQ ID NO: 4; (d) an HVR-L1 comprising the amino acid sequence of SEQ ID NO: 9; (e) an HVR-L2 comprising the amino acid sequence of SEQ ID NO: 10; and (f) an HVR-L3 comprising the amino acid sequence of SEQ ID NO: 11. In some instances, these anti-OX40 antibodies include the following FRs: (a) FR-H1 comprising the amino acid sequence of SEQ ID NO: 5; (b) FR-H2 comprising the amino acid sequence of SEQ ID NO: 6; (c) FR-H3 comprising the amino acid sequence of SEQ ID NO: 7; and (d) FR-H4 comprising the amino acid sequence of SEQ ID NO: 8 and may additionally or alternatively include (e) FR-L1 comprising the amino acid sequence SEQ ID NO: 12; (f) FR-L2 comprising the amino acid sequence of SEQ ID NO: 13; (g) FR-L3 comprising the amino acid sequence of SEQ ID NO: 14; and (h) FR-L4 comprising the amino acid sequence of SEQ ID NO: 15.

In some instances, the anti-OX40 antibodies that bind to amino acid residues 266-277 of OX40 may also include a heavy chain variable domain (VH) sequence having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 16. In certain embodiments, a VH sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 16), but an anti-OX40 antibody including that sequence retains the ability to bind to OX40. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 16. In certain embodiments, substitutions, insertions, or deletions occur in regions outside the HVRs (i.e., in the FRs). Optionally, the anti-OX40 antibodies include the VH sequence in SEQ ID NO: 16, including post-translational modifications of that sequence. In a particular embodiment, the VH comprises one, two, or three HVRs selected from: (a) HVR-H1 comprising the amino acid sequence of SEQ ID NO: 2, (b) HVR-H2 comprising the amino acid sequence of SEQ ID NO: 3, and (c) HVR-H3 comprising the amino acid sequence of SEQ ID NO: 4.

In some instances, the anti-OX40 antibodies that bind to amino acid residues 266-277 of OX40 may also include a light chain variable domain (VL) having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 17. In certain embodiments, a VL sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 17), but an anti-OX40 antibody including that sequence retains the ability to bind to OX40. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 17. In certain embodiments, the substitutions, insertions, or deletions occur in regions outside the HVRs (i.e., in the FRs). Optionally, the anti-OX40 antibody comprises the VL sequence in SEQ ID NO: 17, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In some instances, the anti-OX40 antibodies that bind to amino acid residues 266-277 of OX40 include both VH and VL sequences having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequences of, the amino acid sequences of SEQ ID NOs: 16 and 17, respectively, and may or may not include post-translational modifications of those sequences.

In other instances, the invention provides antibodies that specifically bind OX40, wherein the antibodies include (a) an HVR-H1 comprising the amino acid sequence of SEQ ID NO: 2; (b) an HVR-H2 comprising the amino acid sequence of SEQ ID NO: 3; (c) an HVR-H3 comprising the amino acid sequence of SEQ ID NO: 4; (d) an HVR-L1 comprising the amino acid sequence of SEQ ID NO: 9; (e) an HVR-L2 comprising the amino acid sequence of SEQ ID NO: 10; and (f) an HVR-L3 comprising the amino acid sequence of SEQ ID NO: 11. In some instances, these anti-OX40 antibodies include the following FRs: (a) FR-H1 comprising the amino acid sequence of SEQ ID NO: 5; (b) FR-H2 comprising the amino acid sequence of SEQ ID NO: 6; (c) FR-H3 comprising the amino acid sequence of SEQ ID NO: 7; and (d) FR-H4 comprising the amino acid sequence of SEQ ID NO: 8 and may additionally or alternatively include (e) FR-L1 comprising the amino acid sequence of SEQ ID NO: 12; (f) FR-L2 comprising the amino acid sequence of SEQ ID NO:

13; (g) FR-L3 comprising the amino acid sequence of SEQ ID NO: 14; and (h) FR-L4 comprising the amino acid sequence of SEQ ID NO: 15. In some embodiments, for example, the anti-OX40 antibodies include both a VH and a VL sequence including the sequences of the amino acid sequences of SEQ ID NOs: 16 and 17, respectively, and may or may not include post-translational modifications.

For example, the invention features anti-OX40 antibodies, such as the anti-OX40 antibody SP197, with the following heavy and light chain variable region sequences.

The amino acid sequence of the heavy chain variable region is the following (HVR sequences underlined):

(SEQ ID NO: 16)
QSLEESGGRLVAPGGSLTLTCTVSGIDLS<u>SDNIQ</u>WVRQAPGK
GLEWIGA<u>VDYNNKPFYANWAK</u>GRFTISKTSSTTVDLKMTSL
TTEDTATYFCA<u>KNTFSP</u>WGPGTLVTVSS

The amino acid sequence of the light chain variable region is the following (HVR sequences underlined):

(SEQ ID NO: 17)
DPAMTQTPSSTSAAVGGTVTINC<u>QSSQSVYNANHLS</u>WFQQK
PGQPPKRLIY<u>YISTPDS</u>GVPPRFSGSGSGTQFTLTISGVQCDDA
ATYYC<u>AALNSDEVFT</u>FGGGTEVVVK

In some instances, anti-OX40 antibodies of the invention are antibodies that compete for binding to OX40 with any one or more of the anti-OX40 antibodies described above. In some instances, anti-OX40 antibodies of the invention are antibodies that bind to the same epitope or substantially the same epitope as any one or more of the anti-OX40 antibodies described above.

In some instances, an anti-OX40 antibody according to any of the above embodiments may be a monoclonal antibody, comprising a chimeric, humanized, or human antibody. In one embodiment, an anti-OX40 antibody is an antibody fragment, for example, a Fv, Fab, Fab', scFv, diabody, or F(ab')₂ fragment. In another embodiment, the antibody is a full-length antibody, e.g., an intact IgG antibody (e.g., an intact IgG1 antibody) or other antibody class or isotype as defined herein.

It should be understood that the anti-OX40 antibodies of the invention, although useful for the detection of the presence or the expression level of OX40 in a biological sample as exemplified by the Examples below, may also be used or adapted for therapeutic use.

In further aspects, the anti-OX40 antibodies according to any of the above embodiments may incorporate any of the features, singly or in combination, as described in Sections 1-5 below.

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. *J. Mol. Biol.* 293: 865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al. *Cancer Res.* 57: 4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20™) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al. *J. Mol. Biol.* 293: 865-881, 1999. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9: 129-134, 2003. For a review of scFv fragments, see, e.g., Pluckthun. *The Pharmacology of Monoclonal Antibodies.* Vol. 113, pp. 269-315, Rosenburg and Moore eds. Springer-Verlag, New York, 1994; see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. Nat. Med. 9: 129-134, 2003; and Hollinger et al. Proc. Natl. Acad. Sci. USA. 90: 6444-6448, 1993. Triabodies and tetrabodies are also described in Hudson et al. Nat. Med. 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody.

Certain chimeric antibodies are described, e.g., in U.S. Pat. No. 4,816,567; and Morrison et al. Proc. Natl. Acad. Sci. USA. 81: 6851-6855, 1984. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and 1-Rs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro et al. Front. Biosci. 13: 1619-1633, 2008, and are further described, e.g., in Riechmann et al. Nature. 332: 323-329, 1988; Queen et al. Proc. Natl. Acad. Sci. USA. 86: 10029-10033, 1989; U.S. Pat. Nos. 5,821,337, 7,527,791, 6,982,321, and 7,087,409; Kashmiri et al. Methods. 36: 25-34, 2005 (describing SDR (a-CDR) grafting); Padlan. Mol. Immunol. 28: 489-498, 1991 (describing "resurfacing"); DaU'Acqua et al. Methods. 36: 43-60, 2005 (describing "FR shuffling"); and Osbourn et al. Methods 36: 61-68, 2005 and Klimka et al. Br. J. Cancer. 83: 252-260, 2000 (describing the "guided selection" approach to FR shuffling).

Human framework regions that may be used for humanization include but are not limited to: framework regions selected using the "best-fit" method (see, e.g., Sims et al. J. Immunol. 151: 2296, 1993); framework regions derived from the consensus sequence of human antibodies of a particular subgroup of light or heavy chain variable regions (see, e.g., Carter et al. Proc. Natl. Acad. Sci. USA. 89: 4285, 1992; and Presta et al. J. Immunol. 151: 2623, 1993); human mature (somatically mutated) framework regions or human germline framework regions (see, e.g., Almagro et al. Front. Biosci. 13: 1619-1633, 2008); and framework regions derived from screening FR libraries (see, e.g., Baca et al. J. Biol. Chem. 272: 10678-10684, 1997 and Rosok et al. J. Biol. Chem. 271: 22611-22618, 1996).

4. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for OX40 and the other is for any other antigen. In certain embodiments, bispecific antibodies may bind to two different epitopes of OX40. Bispecific antibodies may also be used to localize cytotoxic agents to cells which express OX40. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein et al. Nature. 305: 537, 1983, WO 93/08829, and Traunecker et al. EMBO J. 10: 3655, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al. Science. 229: 81, 1985); using leucine zippers to produce bi-specific antibodies (see, e.g., Kostelny et al. J. Immunol. 148(5): 1547-1553, 1992; using "diabody" technology for making bispecific antibody fragments (see, e.g., Hollinger et al. Proc. Natl. Acad. Sci. USA., 90: 6444-6448, 1993); and using single-chain Fv (sFv) dimers (see, e.g. Gruber et al. J. Immunol. 152: 5368, 1994); and preparing trispecific antibodies as described, e.g., in Tutt et al. J. Immunol. 147: 60, 1991. Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to OX40 as well as another, different antigen (see, e.g., US 2008/0069820).

5. Antibody Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury. *Methods Mol. Biol.* 207: 179-196, 2008), and/or SDRs (a-CDRs), with the resulting variant VH or VL being tested for binding affinity. Affinity maturation by constructing and reselecting from secondary libraries has been described, e.g., in Hoogenboom et al. *Methods in Molecular Biology.* 178: 1-37, O'Brien et al. eds., Human Press, Totowa, N.J., 2001. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham et al. *Science.* 244: 1081-1085, 1989. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH.* 15: 26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65%, or from 20% to 40%. The amount of fucose is determined by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249, 2004; and Yamane-Ohnuki et al. *Biotech. Bioeng.* 87: 614, 2004. Examples of cell lines capable of producing defucosylated antibodies include Lec13 CHO cells deficient in protein fucosylation (Ripka et al. *Arch. Biochem. Biophys.* 249: 533-545, 1986; US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. Biotech. Bioeng. 87: 614, 2004; Kanda et al. *Biotechnol. Bioeng.* 94(4): 680-688, 2006; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an anti-OX40 antibody of the invention (e.g., SP197) provided herein, thereby generating an Fc region variant. The Fc region variant may comprise a human Fc region sequence (e.g., a human IgG$_1$, IgG$_2$, IgG$_3$ or IgG$_4$ Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch et al. *Annu. Rev. Immunol.* 9: 457-492, 1991. Non-limiting examples of in vitro assays to assess ADCC activity of a molecule of interest is described in U.S. Pat. Nos. 5,500,362 and 5,821,337; Hellstrom et al. *Proc. Natl. Acad. Sci. USA.* 83: 7059-7063, 1986; Hellstrom et al. *Proc. Natl Acad. Sci. USA.* 82: 1499-1502, 1985; and Bruggemann et al. *J. Exp. Med.* 166: 1351-1361, 1987. Alternatively, non-radioactive assays methods may be employed (see, for example, ACTI™ non-radioactive cytotoxicity assay for flow cytometry (CellTechnology, Inc. Mountain View, Calif.; and Cyto-Tox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Natl. Acad. Sci. USA.* 95:652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods.* 202: 163, 1996; Cragg et al. *Blood.* 101: 1045-1052, 2003; and Cragg et al. *Blood* 103: 2738-2743, 2004. FcRn binding and in vivo clearance/half life determinations can also be performed using methods known in the art (see, e.g., Petkova et al. *Intl. Immunol.* 18(12): 1759-1769, 2006).

Antibodies with reduced effector function include those with substitution of one or more of Fc region residues 238, 265, 269, 270, 297, 327, and 329 (U.S. Pat. No. 6,737,056). Such Fc mutants include Fc mutants with substitutions at two or more of amino acid positions 265, 269, 270, 297, and 327, including the so-called "DANA" Fc mutant with substitution of residues 265 and 297 to alanine (U.S. Pat. No. 7,332,581).

Certain antibody variants with improved or diminished binding to FcRs are described. See, e.g., U.S. Pat. No. 6,737,056; WO 2004/056312; and Shields et al. *J. Biol. Chem.* 9(2): 6591-6604, 2001.

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184, 2000.

Antibodies with increased half lives and improved binding to the neonatal Fc receptor (FcRn), which is responsible for the transfer of maternal IgGs to the fetus (Guyer et al. *J. Immunol.* 117: 587, 1976 and Kim et al, *J. Immunol.* 24: 249, 1994), are described in US Patent Application No. 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424, or 434, e.g., substitution of Fc region residue 434 (U.S. Pat. No. 7,371,826). See also Duncan et al. Nature. 322:738-740, 1988; U.S. Pat. Nos. 5,648,260 and 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

e) Antibody Derivatives

In certain embodiments, an anti-OX40 antibody of the invention (e.g., SP197) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. Proc. Natl. Acad. Sci. USA. 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-OX40 antibody described herein (e.g., SP197) is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-OX40 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-OX40 antibody (e.g., SP197), nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. See also Charlton. Methods in Molecular Biology. Vol. 248, pp. 245-254, B. K. C. Lo, ed., Humana Press, Totowa, N.J., 2003, describing expression of antibody fragments in E. coli. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross. Nat. Biotech. 22: 1409-1414, 2004 and Li et al. Nat. Biotech. 24: 210-215, 2006.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40

(COS-7); human embryonic kidney line (293 or 293 cells as described, e.g., in Graham et al. *J. Gen Virol.* 36:59, 1977); baby hamster kidney cells (BHK); mouse Sertoli cells (TM4 cells as described, e.g., in Mather. *Biol. Reprod.* 23:243-251, 1980); monkey kidney cells (CV1); African green monkey kidney cells (VERO-76); human cervical carcinoma cells (HELA); canine kidney cells (MDCK; buffalo rat liver cells (BRL 3 A); human lung cells (W138); human liver cells (Hep G2); mouse mammary tumor (MMT 060562); TRI cells, as described, e.g., in Mather et al. *Annals N.Y. Acad. Sci.* 383:44-68, 1982; MRC 5 cells; and FS4 cells. Other useful mammalian host cell lines include Chinese hamster ovary (CHO) cells, including DHFR" CHO cells (Urlaub et al. *Proc. Natl. Acad. Sci. USA.* 77: 4216, 1980); and myeloma cell lines such as Y0, NS0 and Sp2/0. For a review of certain mammalian host cell lines suitable for antibody production, see, e.g., Yazaki et al. *Methods in Molecular Biology.* Vol. 248, pp. 255-268, B. K. C. Lo, ed., Humana Press, Totowa, N.J., 2003.

C. Assays

Anti-OX40 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, immunohistochemistry, immunofluorescence, etc.

In another aspect, competition assays may be used to identify an antibody that competes with any one of the antibodies of the invention for binding to OX40 (e.g., anti-OX40 antibody SP197). In certain embodiments, such a competing antibody binds to the same epitope (e.g., a linear or a conformational epitope) that is bound by any one of the antibodies of the invention (e.g., anti-OX40 antibody SP197). Detailed exemplary methods for mapping an epitope to which an antibody binds are provided in Morris "Epitope Mapping Protocols," in *Methods in Molecular Biology* Vol. 66 (Humana Press, Totowa, N.J., 1996).

In an exemplary competition assay, immobilized OX40 is incubated in a solution comprising a first labeled antibody that binds to OX40 (e.g., anti-OX40 antibody SP197) and a second unlabeled antibody that is being tested for its ability to compete with the first antibody for binding to OX40. The second antibody may be present in a hybridoma supernatant. As a control, immobilized OX40 is incubated in a solution comprising the first labeled antibody but not the second unlabeled antibody. After incubation under conditions permissive for binding of the first antibody to OX40, excess unbound antibody is removed, and the amount of label associated with immobilized OX40 is measured. If the amount of label associated with immobilized OX40 is substantially reduced in the test sample relative to the control sample, then that indicates that the second antibody is competing with the first antibody for binding to OX40. See, e.g., Harlow et al. Antibodies: A Laboratory Manual. Ch. 14 (Cold Spring Harbor Laboratory, Cold Spring Harbor, N.Y., 1988).

2. Detection Assays

In one aspect, assays are provided for identifying anti-OX40 antibodies useful for detecting the presence of OX40, e.g., in immunohistochemistry (IHC) or immunofluorescence (IF) assays. In certain embodiments, an antibody of the invention is tested for such activity.

D. Immunoconjugates

The invention also provides immunoconjugates comprising an anti-OX40 antibody herein conjugated to one or more labels and/or agents, such as radioactive isotopes.

In one embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an anti-OX40 antibody and label or agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the label or agent. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

E. Methods, Kits, and Compositions for Diagnostics and Detection

In certain embodiments, the anti-OX40 antibodies provided herein (e.g., SP197) are useful for detecting the presence of OX40 in a biological sample. The term "detecting" as used herein encompasses quantitative or qualitative detection.

In one instance, an anti-OX40 antibody (e.g., SP197) for use in a method of diagnosis or detection is provided. In one instance, for example, a method of detecting the presence of OX40 in a biological sample, described below, is provided. In certain embodiments, the method comprises contacting the biological sample with an anti-OX40 antibody as described herein under conditions permissive for binding of the anti-OX40 antibody to OX40, and detecting whether a complex is formed between the anti-OX40 antibody and OX40. Such method may be an in vitro or in vivo method. Anti-OX40 antibodies of the invention (e.g., SP197) can be used, for example, in immunoassays, including, for example, immunohistochemistry (IHC), immunofluorescence (IF), immunoblotting (e.g., Western blotting), flow cytometry, and Enzyme-linked Immunosorbant Assay (ELISA). In one embodiment, an anti-OX40 antibody is used to select subjects eligible for therapy with a cancer immunotherapy, for example, where OX40 is a biomarker for selection of patients.

In certain instances, labeled anti-OX40 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, for example, through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain instances, the anti-OX40 antibodies provided herein are a part of a kit for immunohistochemically detecting the expression of human OX40 in human tissue samples. In an embodiment, the kits include an antibody as described herein and a set of detection reagents. The detection reagents include an antibody capable of binding to the anti-OX40 antibody (termed "secondary antibody"), a detectable entity including an enzyme coupled to or adapted to be coupled to the secondary antibody, and reagents reactive with the enzyme to deposit a chromogen or fluorophore on the sample. In an embodiment, the secondary antibody has affinity for immunoglobulins from a specific animal species from which the primary antibody is derived (termed a "species-specific secondary antibody"). In another embodiment, the secondary antibody is reactive with a tag incorporated into the primary antibody, such as an epitope tag located in the primary amino acid sequence of the primary antibody or a hapten coupled to a reactive side chain of the primary antibody. In another embodiment, the enzyme is coupled to the secondary antibody via a signal amplifier. Signal amplification methods for IHC are known to one of ordinary skill in the art. In some examples, signal amplification includes CAtalyzed Reporter Deposition (CARD), also known as Tyramide Signal Amplification (TSA™). In one variation of this method an enzyme-conjugated secondary antibody (such as an HRP-conjugated secondary antibody) binds to the primary antibody. Next a substrate of biotinylated tyramide (tyramine is 4-(2-aminoethyl)phenol) is used, which presumably becomes a free radical when interacting with the HRP enzyme. The phenolic radical then reacts quickly with the surrounding material, thus depositing or fixing biotin in the vicinity. This process is repeated by providing more substrate (biotinylated tyramide) and building up more localized biotin. Finally, the "amplified" biotin deposit is detected with streptavidin attached to a fluorescent molecule. Alternatively, the amplified biotin deposit can be detected with avidin-peroxidase complex, which is then contacted with DAB to produce a brown color. In other examples, signal amplification includes contacting the sample with hydrogen peroxide and a tyramide-HQ conjugate after contacting the sample with an HRP-conjugated tertiary antibody under conditions sufficient for depositing HQ at or near the site of the primary antibody bound to the sample. The sample is then contacted with an enzyme-conjugated antibody (such as an HRP- or AP-conjugated antibody) that specifically binds to HQ. In some examples, this enzyme-conjugated antibody is the same as the HRP-conjugated tertiary antibody. In other examples, the enzyme-conjugated antibody is a different antibody than the HRP-conjugated tertiary antibody. The sample is then contacted with one or more reagents that produce a detectable reaction product in the presence of the enzyme. In some examples, the sample is contacted with an HRP substrate (such as hydrogen peroxide) and a chromogen (such as DAB) that produces a visually detectable product in the presence of HRP. In some examples, signal amplification is carried out using VENTANA OptiView Amplification Kit (Ventana Medical Systems, Inc., Catalog No. 760-099).

It is also understood that any of the above methods for diagnosis and/or detection may be carried out using an immunoconjugate of the invention, as described above, in place of or in addition to an unconjugated anti-OX40 antibody.

F. Biological Samples

In certain embodiments, the anti-OX40 antibodies of the invention (e.g., SP197) can be used to detect the presence of OX40 in biological samples using methods known in the art or described herein.

In some instances a biological sample includes a tissue or a cell sample. For example, a biological sample may include a cell or tissue from normal or cancer patients, such as, for example, normal and cancerous tissue of breast, colon, lung, kidney, bone, brain, muscle, stomach, pancreas, bladder, ovary, uterus, as well as heart, embryonic, and placental tissue.

In certain instances the source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments the biological sample is obtained from in vitro tissue or cell culture. Examples of biological samples herein include, but are not limited to, tumor biopsies, circulating tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded (FFPE) tumor samples or frozen tumor samples.

In some embodiments the biological sample contains compounds which are not naturally intermixed with the tissue in nature such as preservatives, anticoagulants, buffers, nutrients, antibiotics, or the like. In certain embodiments the biological sample has been exposed to and/or contains one or more fixatives. Fixatives that can be used with methods and compositions of the invention include formalin, glutaraldehyde, osmium tetraoxide, acetic acid, ethanol, acetone, picric acid, chloroform, potassium dichromate and mercuric chloride and/or stabilizing by microwave heating or freezing.

In some embodiments, the biological sample is from a subject having, predisposed to, or being tested for an autoimmune disease. In certain embodiments, the autoimmune disease is an autoimmune rheumatologic disorder (including rheumatoid arthritis, Sjogren's syndrome, scleroderma, lupus such as SLE and lupus nephritis, polymyositis-dermatomyositis, cryoglobulinemia, anti-phospholipid antibody syndrome, and psoriatic arthritis), an autoimmune gastrointestinal and liver disorder (including inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (including ANCA-negative vasculitis and ANCA-associated vasculitis, including Churg-Strauss vasculitis, Wegener's granulomatosis, and microscopic polyangiitis), an autoimmune neurological disorder (including multiple sclerosis, opsoclonus myoclonus syndrome, myasthenia gravis, neuromyelitis optica, Parkinson's disease, Alzheimer's disease, and autoimmune polyneuropathies), a renal disorder (including glomerulonephritis, Goodpasture's syndrome, and Berger's disease), an autoimmune dermatologic disorder (including psoriasis, urticaria, hives, pemphigus vulgaris, bullous pemphigoid, and cutaneous lupus erythematosus), a hematologic disorder (including thrombocytopenic purpura, thrombotic thrombocytopenic purpura, post-transfusion purpura, and autoimmune hemolytic anemia), atherosclerosis, uveitis, an autoimmune hearing disease (including inner ear disease and hearing loss), Behcet's disease, Raynaud's syndrome, organ transplant, or an autoimmune endocrine disorder (including diabetic-related autoimmune diseases such as insulin-dependent diabetes mellitus (IDDM), Addison's disease, and autoimmune thyroid disease (including Graves' disease and thyroiditis)).

In other embodiments, the biological sample is from a subject having, predisposed to, or being tested for cancer. In certain embodiments the cancer is carcinoma, lymphoma (including Hodgkin's and non-Hodgkin's lymphoma), blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, or various types of head and neck cancer. In a specific embodiment, the cancer is selected from non-small cell lung cancer (NSCLC), bladder cancer, renal cell carcinoma (RCC), ovarian cancer, colorectal cancer, triple negative breast cancer (TNBC), and melanoma.

III. EXAMPLES

The following are examples of methods and compositions of the invention. It is understood that various other embodiments may be practiced, given the general description provided above.

Example 1. Generation of Anti-OX40 Antibodies

Anti-OX40 rabbit monoclonal antibodies were generated as schematically depicted in FIG. 1. Briefly, the peptide fragment of amino acid residues 266-277 of was synthesized. The 12-amino acid fragment intended for immunization was conjugated to keyhole limpet hemocyanin (KLH), an extensively used carrier protein for stimulating a substantial immune response via antibody production. New Zealand White rabbits were immunized with KLH conjugated OX40 antigen emulsified with complete Freund's adjuvant followed by a series of OX40 antigen booster emulsified with incomplete Freund's adjuvant. The antibody-expressing cells were screened by enzyme-linked immunoabsorbant assay (ELISA) using the OX40 antigen. All ELISA positive clones were further screened by immunohistochemistry (IHC), and the clone producing the antibody with the highest specificity was selected. For recombinant production of anti-OX40 antibodies, cDNA coding for the heavy chain and light chain sequences of the antibodies were cloned, expressed by co-transfection, and screened for binding to OX40 by IHC. Anti-OX40 monoclonal antibody SP197 was produced using these methods and subsequently purified by Protein A affinity chromatography. The heavy and light chain variable region sequences of the SP197 antibody are as follows.

The amino acid sequence of the heavy chain variable region is the following (HVR sequences underlined):

```
                                          (SEQ ID NO: 16)
QSLEESGGRLVAPGGSLTLTCTVSGIDLSSDNIQWVRQAPGK

GLEWIGAVDYNNKPFYANWAKGRFTISKTSSTTVDLKMTSL

TTEDTATYFCAKNTFSPWGPGTLVTVSS
```

The amino acid sequence of the light chain variable region is the following (HVR sequences underlined):

```
                                          (SEQ ID NO: 17)
DPAMTQTPSSTSAAVGGTVTINCQSSQSVYNANHLSWFQQK

PGQPPKRLIYYISTPDSGVPPRFSGSGSGTQFTLTISGVQCDDA

ATYYCAALNSDEVFTFGGGTEVVVK
```

Example 2. Diagnostic Uses of Anti-OX40 Antibodies

Specific immunohistochemical (IHC) staining of rabbit anti-human OX-40 monoclonal antibody (SP197) on control cells and FFPE tissues has been demonstrated. IHC was performed using StdCC1 cell conditioning with ultraView Universal DAB Detection Kit (Ventana Medical Systems, Inc., Tucson, Ariz.). Primary antibody was incubated for 16 min at 37° C. on a BenchMark ULTRA automated slide stainer (Ventana Medical Systems, Inc., Tucson, Ariz.). Results are shown at Fig. (A) Mock transfected cells (negative control cells); (B) OX-40 transfected cells (positive control cells); (C) Reactive lymph node; and (D) Prostate adenocarcinoma. Strong membrane staining was seen in positive control cells (B) and activated T-cells in reactive lymph node and prostate adenocarcinoma.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An isolated antibody capable of specifically binding to a C-terminal portion of OX40 comprising amino acids 266-277 of SEQ ID NO: 1, wherein the antibody comprises a heavy chain variable domain (VH) sequence comprising the following heavy chain hypervariable regions (HVR-H):
   (a) an HVR-H1 comprising the amino acid sequence of SEQ ID NO: 2;
   (b) an HVR-H2 comprising the amino acid sequence of SEQ ID NO: 3;
   (c) an HVR-H3 comprising the amino acid sequence of SEQ ID NO: 4; and and a light chain variable domain (VL) sequence comprising the following light chain hypervariable regions (HVR-L):
   (d) an HVR-L1 comprising the amino acid sequence of SEQ ID NO: 9;
   (e) an HVR-L2 comprising the amino acid sequence of SEQ ID NO: 10; and
   (f) an HVR-L3 comprising the amino acid sequence of SEQ ID NO: 11.

2. The antibody of claim 1, wherein the VH sequence further comprises the following heavy chain variable domain framework regions (FR-Hs):
   (g) FR-H1 comprising the amino acid sequence of SEQ ID NO: 5;
   (h) FR-H2 comprising the amino acid sequence of SEQ ID NO: 6;
   (i) FR-H3 comprising the amino acid sequence of SEQ ID NO: 7; and
   (j) FR-H4 comprising the amino acid sequence of SEQ ID NO: 8.

3. The antibody of claim 1, wherein the VL sequence further comprises the following light chain variable domain FRs:
   (k) FR-L1 comprising the amino acid sequence of SEQ ID NO: 12;
   (l) FR-L2 comprising the amino acid sequence of SEQ ID NO: 13;
   (m) FR-L3 comprising the amino acid sequence of SEQ ID NO: 14; and
   (n) FR-L4 comprising the amino acid sequence of SEQ ID NO: 15.

4. The antibody of claim 1, wherein:
   the VH sequence has at least 95% sequence identity to the amino acid sequence of SEQ ID NO: 16; or
   the VL sequence has at least 95% sequence identity to the amino acid sequence of SEQ ID NO: 17; or
   the VH sequence has at least 95% sequence identity to the amino acid sequence of SEQ ID NO: 16 and the VL sequence has at least 95% sequence identity to the amino acid sequence of SEQ ID NO: 17.

5. The antibody of claim 1, wherein the VH sequence comprises SEQ ID NO: 16.

6. The antibody of claim 1, wherein the VL sequence comprises SEQ ID NO: 17.

7. The antibody of claim 1, wherein the antibody further comprises the following heavy chain variable domain framework regions (FR-Hs) and light chain variable domain framework regions (FR-Ls):
   (g) FR-H1 comprising the amino acid sequence of SEQ ID NO: 5;
   (h) FR-H2 comprising the amino acid sequence of SEQ ID NO: 6;
   (i) FR-H3 comprising the amino acid sequence of SEQ ID NO: 7;
   (j) FR-H4 comprising the amino acid sequence of SEQ ID NO: 8;
   (k) FR-L1 comprising the amino acid sequence of SEQ ID NO: 12;
   (l) FR-L2 comprising the amino acid sequence of SEQ ID NO: 13;
   (m) FR-L3 comprising the amino acid sequence of SEQ ID NO: 14; and
   (n) FR-L4 comprising the amino acid sequence of SEQ ID NO: 15.

8. The antibody of claim 1, wherein the antibody comprises a VH sequence of SEQ ID NO: 16 and a VL sequence of SEQ ID NO: 17.

9. The antibody claim 1, wherein the antibody is a monoclonal antibody.

10. The antibody of claim 9, wherein the monoclonal antibody is a rabbit monoclonal antibody.

11. The antibody of claim 1, wherein the antibody is an IgG antibody.

12. The antibody of claim 1, wherein the antibody is an antibody fragment that specifically binds OX40.

13. The antibody of claim 12, wherein the antibody fragment is selected from the group consisting of Fab, single chain variable fragment (scFv), Fv, Fab', Fab'-SH, F(ab')2, and diabody.

14. A kit comprising an antibody according to claim 1.

15. The kit of claim 14, further comprising a secondary antibody immunoreactive with the antibody capable of specifically binding to the C-terminal portion of OX40.

16. The kit of claim 15, further comprising an enzyme coupled to or adapted to be coupled to the secondary antibody.

17. The kit of claim 16, further comprising a set of reagents reactive with the enzyme to deposit a chromogen or fluorophore.

18. The kit of claim 17, wherein the set of reagents reactive with the enzyme comprises a tyramide conjugate.

19. A method of detecting the presence or expression level of OX40 in a biological sample comprising contacting the biological sample with the antibody of claim 1 and detecting the presence of the bound antibody.

20. The method of claim 19, wherein the detecting is by immunohistochemistry (IHC), immunofluorescence, or immunoblot.

21. The method of claim 20, wherein the detecting is by IHC.

22. The method of claim 19, wherein the sample comprises a fixed tissue.

23. The method of claim 22, wherein the fixed tissue is a FFPE tissue.

24. The method of claim 19, wherein the sample is from a subject having or predisposed to cancer or autoimmune disease.

* * * * *